(12) United States Patent
Callas et al.

(10) Patent No.: US 8,603,031 B2
(45) Date of Patent: Dec. 10, 2013

(54) METHOD AND SYSTEM FOR ACCESSING A PERICARDIAL SPACE

(75) Inventors: Peter Callas, Castro Valley, CA (US);
Gary L. Hague, Carlsbad, CA (US);
John S. Greenland, San Diego, CA (US); Bruce A. Tockman, Scandia, MN (US); Peter T. Kelley, Buffalo, MN (US); Jason A. Shiroff, Shoreview, MN (US); David B. Yingling, Stillwater, MN (US); Theodore J. Schulte, Austin, TX (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 0 days.

(21) Appl. No.: 13/540,362

(22) Filed: Jul. 2, 2012

(65) Prior Publication Data
US 2013/0006288 A1 Jan. 3, 2013

Related U.S. Application Data

(63) Continuation of application No. 11/159,705, filed on Jun. 23, 2005, now abandoned.

(51) Int. Cl.
*A61M 5/00* (2006.01)
*A61M 5/32* (2006.01)

(52) U.S. Cl.
USPC .......................... 604/115; 604/176; 604/272

(58) Field of Classification Search
USPC ........ 604/21, 22, 51, 53, 96.1, 115, 164, 176, 604/268, 500, 506, 509, 565, 567, 96.01
See application file for complete search history.

(56) References Cited

U.S. PATENT DOCUMENTS

| | | | |
|---|---|---|---|
| 3,833,003 A | 9/1974 | Taricco | |
| 5,817,005 A | 10/1998 | Cohen | |
| 5,827,216 A * | 10/1998 | Igo et al. | 604/21 |
| 5,868,770 A | 2/1999 | Rygaard | |
| 5,931,810 A | 8/1999 | Grabek | |
| 5,972,013 A * | 10/1999 | Schmidt | 606/185 |
| 6,162,195 A | 12/2000 | Igo et al. | |
| 6,206,004 B1 | 3/2001 | Schmidt et al. | |
| 6,231,518 B1 | 5/2001 | Grabek et al. | |
| 6,423,051 B1 | 7/2002 | Kaplan et al. | |
| 6,478,728 B1 | 11/2002 | Wright | |
| 6,592,552 B1 | 7/2003 | Schmidt | |
| 6,666,844 B1 | 12/2003 | Igo et al. | |
| 6,837,848 B2 * | 1/2005 | Bonner et al. | 600/114 |
| 7,186,214 B2 | 3/2007 | Ness | |
| 7,226,440 B2 | 6/2007 | Gelfand et al. | |
| 2002/0095139 A1 | 7/2002 | Keogh et al. | |
| 2002/0138109 A1 | 9/2002 | Keogh et al. | |

(Continued)

*Primary Examiner* — Kevin C Sirmons
*Assistant Examiner* — William Carpenter
(74) *Attorney, Agent, or Firm* — Faegre Baker Daniels LLP

(57) ABSTRACT

A device and method for accessing a pericardial space of the heart includes a shaft having a cavity at a distal end, a suction lumen terminating in a distal port within the cavity and a hollow needle having a distal tip extending into the cavity. The cavity may be a recess in the shaft into which the distal tip of the needle fixedly protrudes. In other embodiments, the cavity is formed by an inflatable member positioned at the distal end of the shaft and the needle is slidable relative to the shaft. Suction is applied at the cavity to draw a pericardial bleb. The needle pierces the pericardial bleb for accessing the pericardial space and also facilitates delivery of payloads into the pericardial space.

14 Claims, 9 Drawing Sheets

(56) References Cited

U.S. PATENT DOCUMENTS

| | | |
|---|---|---|
| 2003/0093104 A1 | 5/2003 | Bonner et al. |
| 2003/0212446 A1 | 11/2003 | Kaplan et al. |
| 2004/0138527 A1 | 7/2004 | Bonner et al. |
| 2004/0138531 A1 | 7/2004 | Bonner et al. |
| 2006/0173441 A1 * | 8/2006 | Gelfand et al. ............... 604/509 |
| 2007/0010793 A1 | 1/2007 | Callas et al. |

* cited by examiner

METHOD AND SYSTEM FOR ACCESSING A PERICARDIAL SPACE

CROSS-REFERENCE TO RELATED APPLICATIONS

This application is a continuation of U.S. application Ser. No. 11/159,705, filed Jun. 23, 2005, which is herein incorporated by reference in its entirety.

TECHNICAL FIELD

The present invention relates to medical devices and methods for accessing an anatomical space of the body. More specifically, the invention relates to devices and methods for accessing the pericardial space of the heart in a minimally-invasive manner.

BACKGROUND

The human heart is enveloped within a tissue structure referred to as the pericardium, which comprises two major parts. The inner layer of the pericardium lies immediately over the myocardium (heart muscle) and is referred to as the visceral pericardium or epicardium. The outer layer, forming a sac around the visceral pericardium, is referred to as the parietal pericardium. Normally these two layers lie in close contact with each other and are separated only by a thin layer of pericardial fluid, which allows the heart to move within the parietal sac with minimal friction. The potential space between the visceral and parietal pericardia is referred to as the pericardial space. The visceral pericardium is commonly referred to as the epicardium and the parietal pericardium is commonly referred to as the pericardium. This naming convention will be used herein.

Access to the pericardial space is necessary for a variety of medical procedures, including treatment of infections, injuries, and heart defects. For example, cardiac rhythm management systems such as pacemakers, implantable pulse generators, and implantable cardioverter defibrillators include electrode bearing leads for sensing and stimulating the heart. These leads can be deployed from inside or outside the heart. In the latter case, the pericardial space is typically traversed to reach the epicardium for lead implantation and attachment.

Part of the challenge in accessing the pericardial space stems from its minimal thickness. When making an incision or perforation in the pericardium, it is preferable to avoid also puncturing the underlying epicardium and damaging the myocardium or a coronary vessel. The close proximity of the epicardium to the pericardium makes this difficult. Another important consideration is the trend toward minimally-invasive surgical techniques, which generally are associated with a host of advantages including lower costs and fewer complications.

There is a need in the art for improved, efficacious methods and devices for penetrating the pericardium and thereby accessing the pericardial space, which minimize the risk of damaging other heart tissues. There is a further need for such methods and devices that are compatible with minimally-invasive surgical techniques.

SUMMARY

According to one embodiment, the present invention is a device for accessing a pericardial space of a heart. The device includes a shaft that extends from a proximal end to a distal end and defines a cavity disposed near the distal end. The shaft further includes a suction lumen terminating in at least one distal suction port located within the cavity. A hollow needle extends through the shaft and is fixed in position relative to a longitudinal axis of the shaft. The needle has a sharp distal end protruding into the cavity toward a heart surface at an angle with respect to a longitudinal axis of the shaft.

According to another embodiment, the present invention is a device for accessing a pericardial space of a heart and includes a shaft extending from a proximal end to a distal end, and having a suction lumen terminating in at least one distal suction port near the distal end and an inflation lumen. An inflatable member is positioned near a distal end of the shaft and has a collapsed configuration and an inflated configuration that defines a cavity. The inflatable member is in communication with the inflation lumen. Finally, the device includes a hollow needle adapted for advancement through the shaft into the cavity.

According to still another embodiment, the present invention is a method of accessing the pericardial space in which a distal end of a shaft is maneuvered to the pericardial surface. An inflatable member disposed at the distal end of the shaft is inflated to an inflated configuration defining a cavity adjacent the pericardial surface. Suction is applied within the cavity to draw the pericardium into the cavity and create an enlarged region. The pericardium within the cavity is pierced to access the pericardial space and a payload is inserted through the pierced pericardium and into the pericardial space.

While multiple embodiments are disclosed, still other embodiments of the present invention will become apparent to those skilled in the art from the following detailed description, which shows and describes illustrative embodiments of the invention. As will be realized, the invention is capable of modifications in various obvious aspects, all without departing from the spirit and scope of the present invention. Accordingly, the drawings and detailed description are to be regarded as illustrative in nature and not restrictive.

Figure 1:
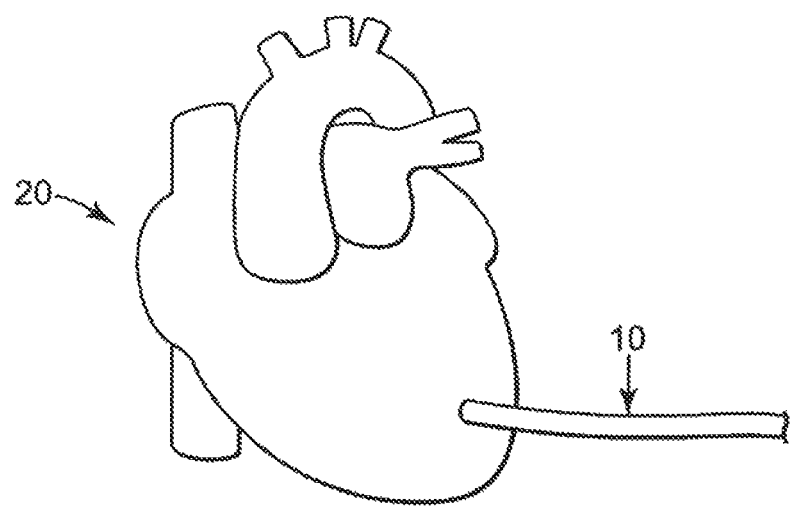
FIG. 1 is a schematic view of a pericardial access system, according to one embodiment of the invention, in relation to a heart.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

FIG. 1 is a general schematic illustration of a pericardial access device 10, in accordance with a first embodiment of the present invention, in relation to a heart 20. As shown in greater detail in the sectional side view of FIG. 2, the pericardial access device 10 is positioned adjacent a pericardium 22 of the heart 20. A pericardial space 24 lies opposite the pericardium 22 and is bounded by an epicardium 26 on its far side. The epicardium 26 contacts a myocardium 28 on the side opposite the pericardial space 24. The pericardial access device 10 may be employed for accessing the pericardial space 24 to facilitate a variety of procedures, including those requiring a minimally invasive approach to the heart 20. Such procedures include, for example, epicardial lead placement, cellular myoplasty, transmyocardial revascularization, epicardial ablation, closed chest coronary anastomosis, epicardial/myocardial drug delivery, diagnoses and pericardicentesis (draining pericardial fluid).

Figure 2:
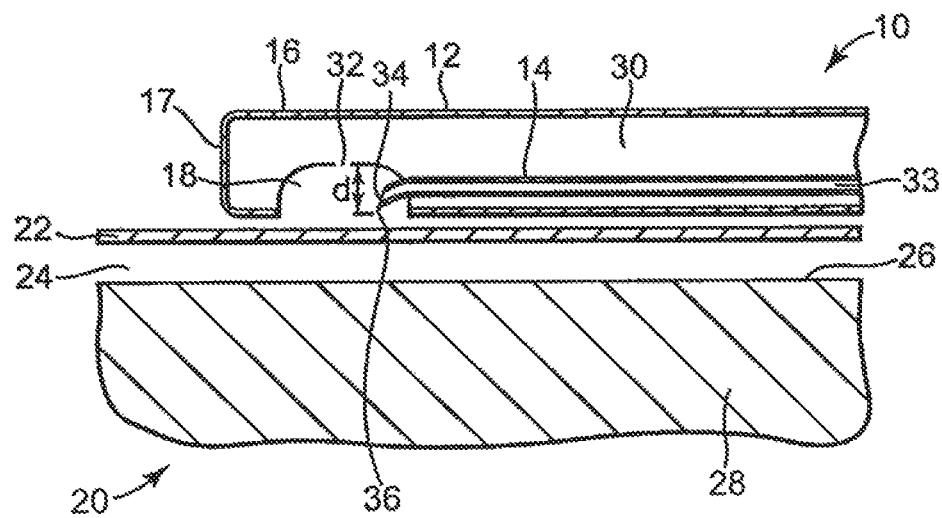
FIG. 2 is a side sectional view of a pericardial access system, according to one embodiment of the invention, in relation to the anatomic layers of the heart.

As shown in FIG. 2, the device 10 includes a shaft 12 and a needle 14 fixed in relation to a longitudinal axis of the shaft 12 (i.e., the needle 14 is prevented from moving longitudinally within the shaft 12). The shaft 12 extends from a proximal end (not shown) to a distal end 16 provided with an atraumatic tip 17. The shaft 12 is sized so that the distal end 16 can be brought into proximity with the pericardium 22 while the proximal end is accessible from outside of the chest cavity. The shaft 12 includes a cavity or recessed region 18 having a depth, d, disposed near the distal end 16, preferably somewhat proximal relative to the distal tip 17 of the shaft 12. A suction lumen 30 extends from a proximal port (not shown) near the proximal end of the shaft adapted for connecting to a source of negative pressure to a suction port 32 disposed at the recessed region 18 of the shaft 12. In other embodiments, the cavity or region 18 includes a plurality of ports 32 distributed at various locations to optimize the suction force applied to the pericardium 22. In one embodiment, the cavity 18 is defined by a substantially concave cavity wall. In other embodiments, the cavity 18 has other shapes and configurations.

The needle 14 is a hollow tubular structure defining an inner bore 33 and having a sharp distal tip 36. The needle tip 36 protrudes into the recessed region 18 of the shaft 12 a fixed distance and, in one embodiment, is angled downwardly, or towards the pericardium 22. However, the needle 14 extends downwardly no further than the depth, d, of the cavity 18, such that the needle tip 36 is wholly located within the cavity 18. This prevents the needle tip 36 from snagging on tissue as the pericardial access device 10 is advanced to the heart 20. The needle 14 includes an access port 34 in fluid communication with the needle bore 33. The access port 34 is located near the needle tip 36 and is positioned within the cavity 18 of the shaft 12. The needle bore 33 and access port 34 are adapted for slidably receiving medical instruments, for example, guidewires, and/or fluids or gases. In one embodiment, the needle 14 extends from about 0.5 to about 3 mm into the cavity 18. In one embodiment, the needle 14 extends downwardly toward the heart at an angle of from about 15 to about 60 degrees with respect to a longitudinal axis of the shaft 12.

As illustrated in FIG. 2, the suction lumen 30 encompasses generally the entire interior of the shaft 12, and the needle 14 is positioned within the suction lumen 30, as is shown in FIG. 2. In other embodiments, the shaft 12 includes a secondary lumen separate from the suction lumen 30 for receiving the needle 14 (see for example FIG. 6), or the needle 13 is integrally formed within the shaft 12.

Figure 3:
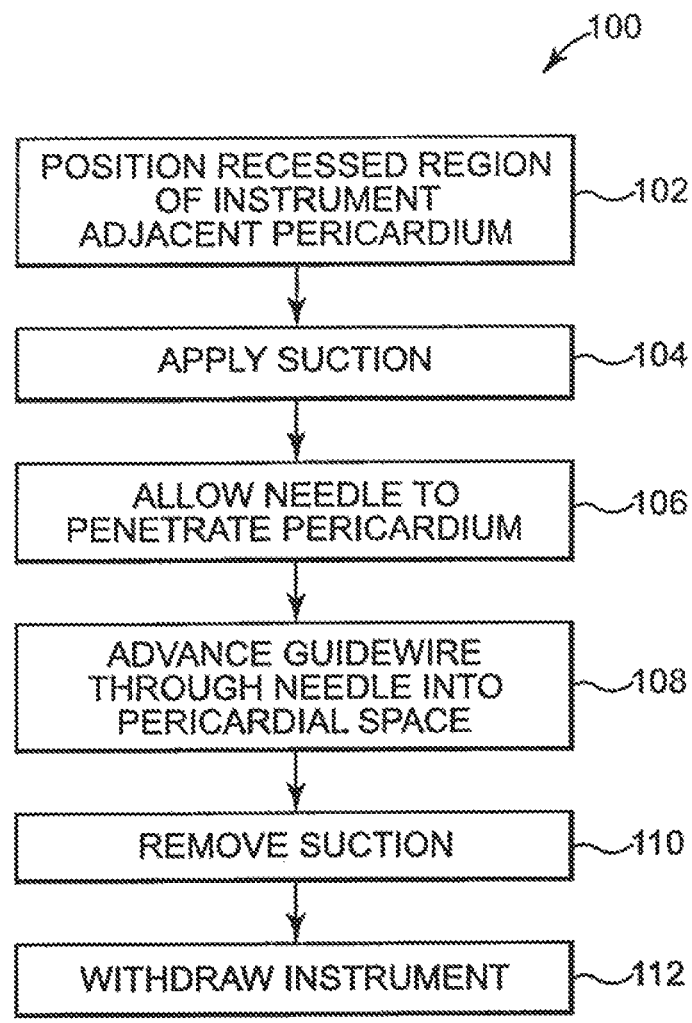
FIG. 3 is a flowchart detailing a method of accessing the pericardial space using the pericardial access system of FIG. 2.
Figure 4:
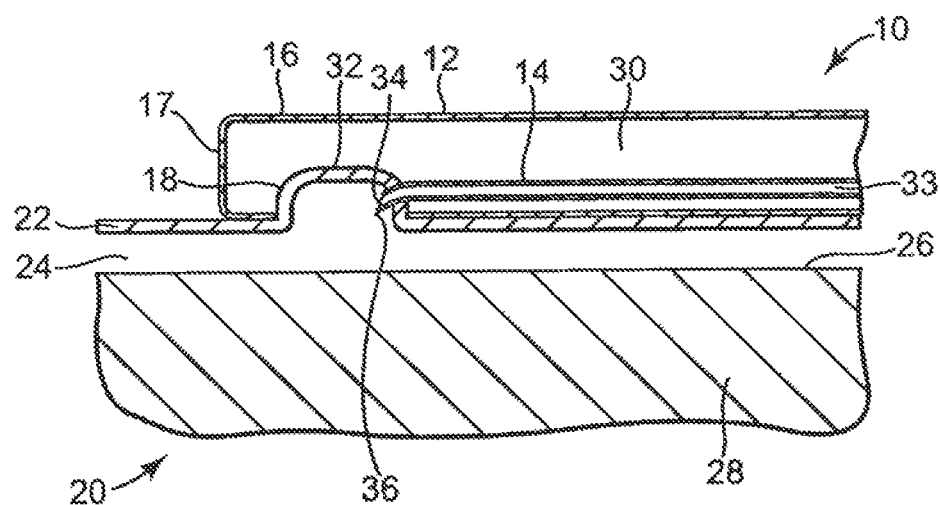
FIG. 4 is a side sectional view of the pericardial access system of FIG. 2 in which negative pressure has been applied.
Figure 5:
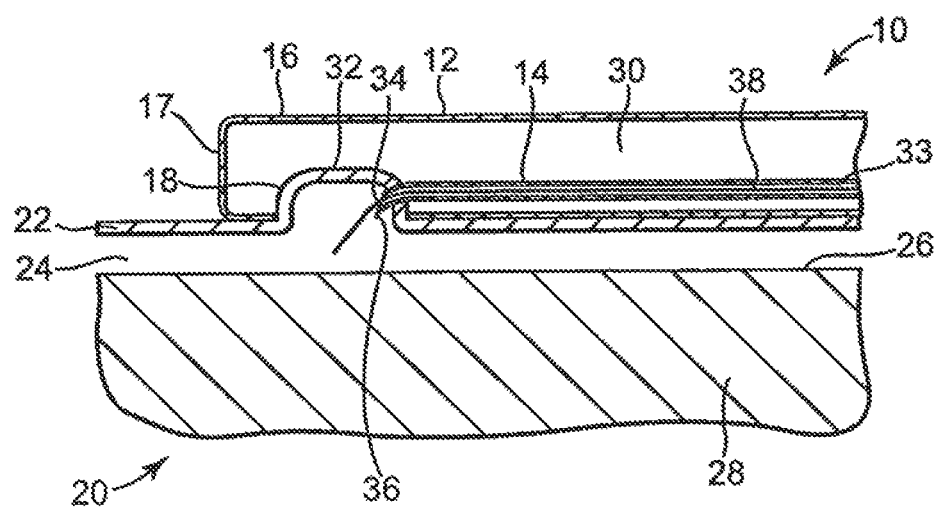
FIG. 5 is a side sectional view of the pericardial access system of FIG. 2 in which the pericardium has been pierced.

FIG. 3 is a flowchart detailing a method 100 of accessing the pericardial space 24 using the pericardial access system 10 of FIG. 2 according to one embodiment of the present invention. The shaft 12 is inserted into the chest by, for example, a sub-xiphoid insertion route, and maneuvered to the pericardium 22 of the heart 20 so that the recessed region 18 is positioned adjacent the pericardium 22 (block 102). Suction or negative pressure is applied to the suction port 32 via the suction lumen 30, drawing the pericardium 22 into the recessed region 18, as is shown in FIG. 4, forming what is known as a pericardial bleb. This increases the volume of the pericardial space 24 at the recessed region 18 (block 104). The negative pressure is sufficient to cause the pericardium 22 to engage the stationary and protruding needle tip 36, such that the needle tip 36 is caused to penetrate the pericardium 22 (block 106), as shown in FIG. 4. The depth, d, of the cavity 18 is sufficient that when the pericardium 22 is drawn upwardly, the needle tip 36 not only penetrates the pericardium 22, but also the access port 34 extends into the pericardial space 24. A payload, such as a guidewire 38, is inserted through the access port 34 via the needle bore 33 and into the pericardial space 24 within the recessed region 18 (block 108), as shown in FIG. 5.

Upon completion of the procedure, the negative pressure is removed, allowing the pericardium 22 to withdraw to a normal position, disengaging from the needle tip 36 (block 110). Finally, the shaft 12 is withdrawn from the pericardium 22 (block 112), with the guidewire 38 remaining in the pericardial space 24. The guidewire 38 may be employed to facilitate the delivery of other instruments, for example, cardiac pacing leads. Alternately, rather than delivering a payload (block 108) the needle 14 may be employed to drain off excess fluid from the pericardial space 24.

In this manner, the pericardial space 24 is accessed without piercing the epicardium 26. As the needle tip 36 is in a fixed position in relation to the recessed region 18, there is no danger of over inserting the needle 14 or of the needle 14 inadvertently snagging on tissues. Furthermore, because it is unnecessary to advance the needle 14 into position after suctioning to the pericardium 22, there is no risk of dislodging the suction port 32 from the pericardium 22.

Figure 6:
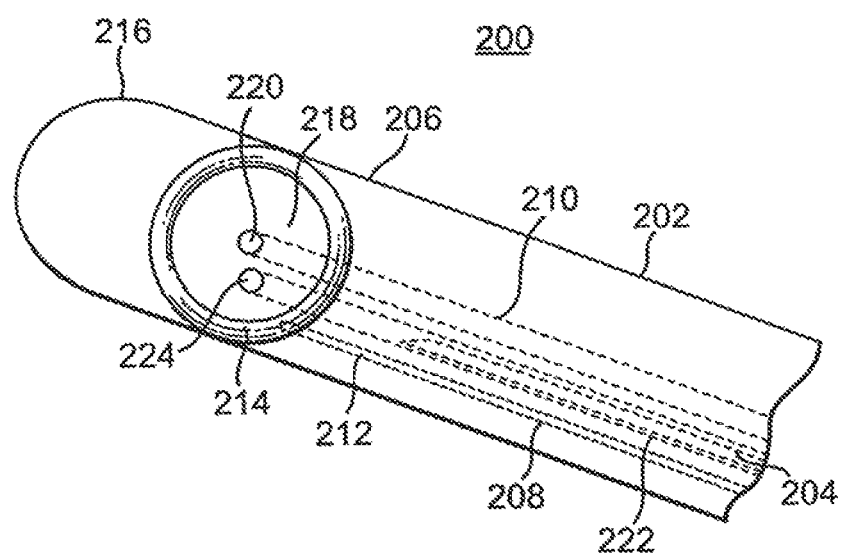
FIG. 6 is a perspective view of the underside of a pericardial access system in accordance with another embodiment of the present invention.

FIG. 6 is a bottom perspective view of a pericardial access device 200 according to another embodiment of the present invention. The pericardial access device 200 includes a shaft 202 and a needle 204 slidably disposed within the shaft 202

(see FIGS. 8-12). The shaft 202 extends from a proximal end (not shown) to a distal end 206 and includes an inflation lumen 208 and a suction lumen 210. The inflation lumen 208 extends from a proximal end adapted for connection to a source of air or fluid pressure (not shown) to a distal end 212 in fluid communication with an inflatable member 214. Inflatable member 214 may be toroidal or ring-shaped, and is disposed on the shaft 202 proximal to an atraumatic distal tip 216 of the shaft 202. The shaft includes a slight recess 215 sized to receive the inflatable member 214 when in a deflated configuration. Inflatable member 214 may have a variety of other shapes, and recess 215 may have a variety of configuration to accommodate inflatable member 214. For example, inflatable member 214 may be elliptical, egg-shaped, elongated, or asymmetric. Particular shapes may be chosen to facilitate forming a sealing engagement with a surface of the heart.

The suction lumen 210 extends from a proximal end adapted for connection to a source of suction or negative pressure (not shown) to a distal end 218 in fluid communication with a suction port 220. The suction port 220 is disposed on the shaft 202 proximal to the distal tip 216 of the shaft 202 and in particular is positioned within the circumference of the inflatable member 214, such that the inflatable member 214 generally surrounds the suction port 220. In one embodiment, the shaft 202 may include multiple suction lumens terminating at various locations within the circumference of the inflatable member 214. The shaft 202 further includes a secondary lumen 222 having a distal port 224 disposed adjacent the suction port 220 within the circumference of the inflatable member 214. Alternately, the secondary lumen 222 and the suction lumen 210 are one in the same (Not shown; see generally the embodiment of FIG. 2). The secondary lumen 222 is adapted for slidably receiving the needle 204, as is shown in FIGS. 8-12.

Figure 7:
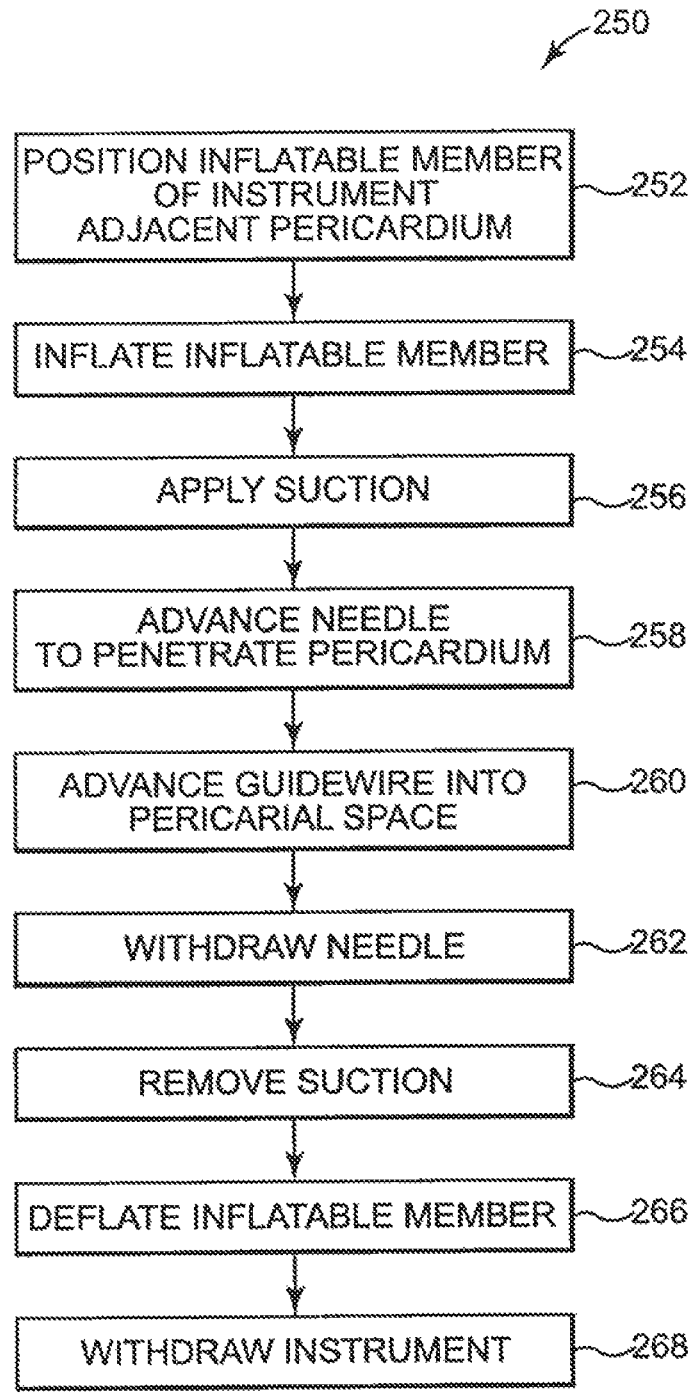
FIG. 7 is a flowchart detailing a method of accessing the pericardial space using the pericardial access system of FIG. 6.
Figure 8:
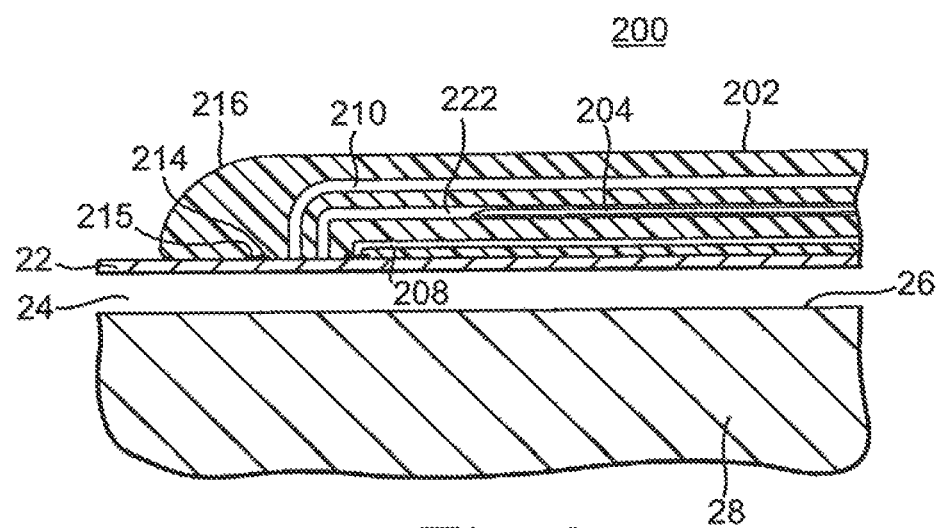
FIG. 8 is a side sectional view of the pericardial access system of FIG. 6 in relation to the anatomic layers of the heart in which the inflatable member is deflated.
Figure 9:
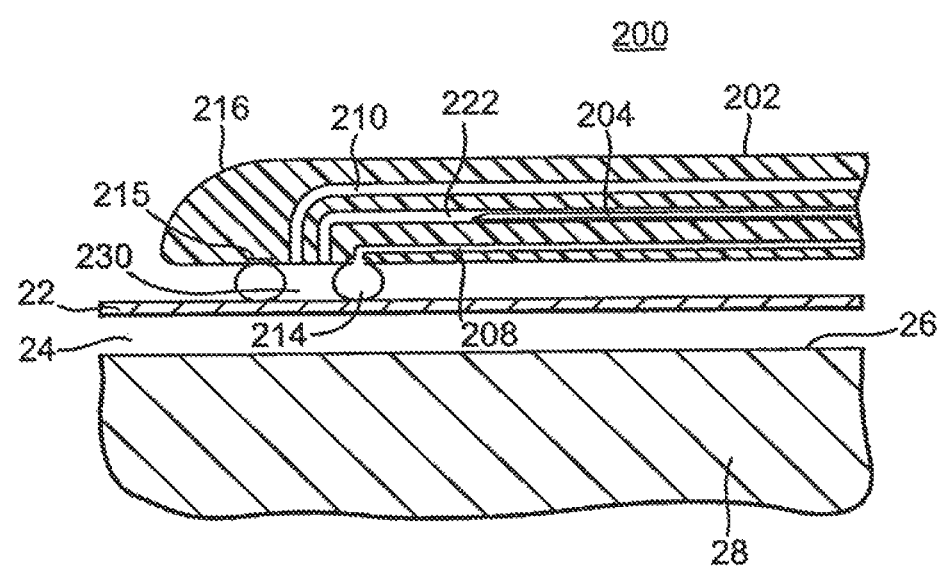
FIG. 9 is a side sectional view of the pericardial access system of FIG. 8 in which the inflatable member is inflated.
Figure 10:
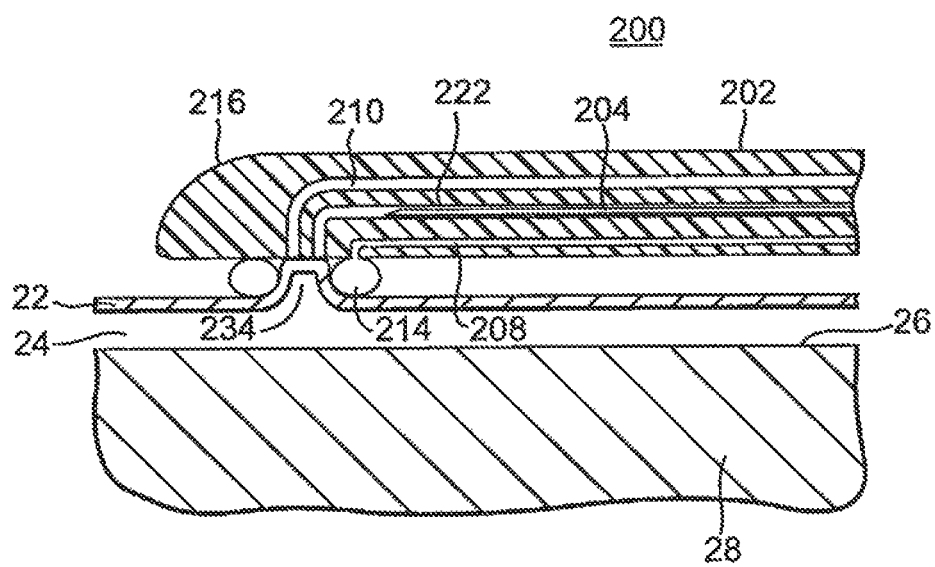
FIG. 10 is a side sectional view of the pericardial access system of FIG. 8 in which negative pressure has been applied.

FIG. 7 is a flowchart detailing a method 250 of accessing the pericardial space 24 using the pericardial access device 200 of FIG. 6, according to one embodiment of the present invention. The shaft 202 is inserted into the chest using, for example, a sub-xiphoid insertion route, and the distal end 206 is brought into proximity with the pericardium 22 so that the inflatable member 214 is positioned adjacent the pericardium 22 (block 252), as shown in FIG. 8. As shown in FIG. 9, the inflatable member 214 is inflated, forming a toroidal or cylindrical-shaped ring adjacent the pericardium 22 (block 254). The inflated inflatable member 214 defines an open space or cavity 230 adjacent the pericardium 22 and causes the suction port 220 to be spaced above the pericardium 22. Negative pressure is then applied to the suction lumen 210, causing the pericardium 22 to be drawn upwardly into the cavity 230 (block 256), as shown in FIG. 10, forming what is known as a pericardial bleb. This increases the volume of a region 234 of the pericardial space 24 adjacent the inflatable member 214.

Figure 11:
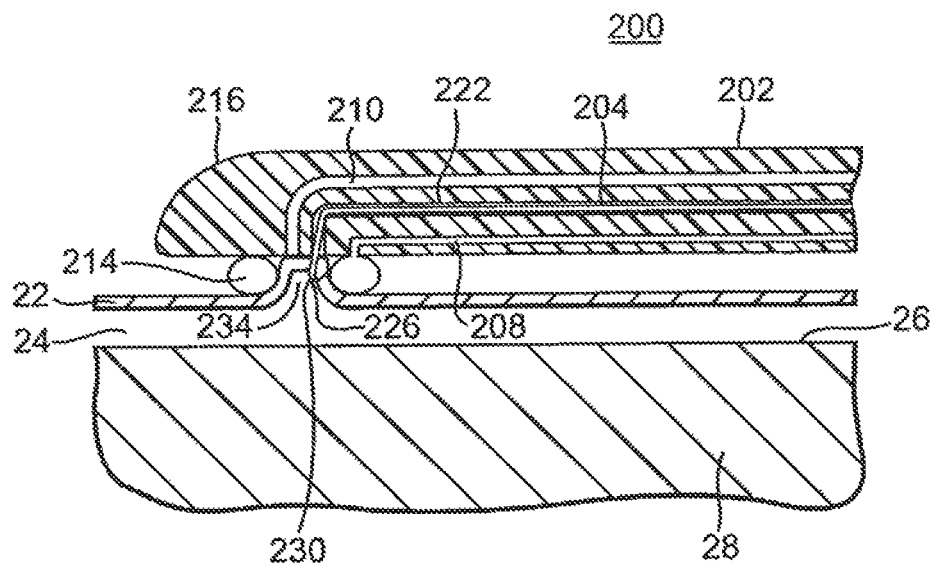
FIG. 11 is a side sectional view of the pericardial access system of FIG. 8 in which a needle has been advanced to pierce the pericardium.
Figure 12:
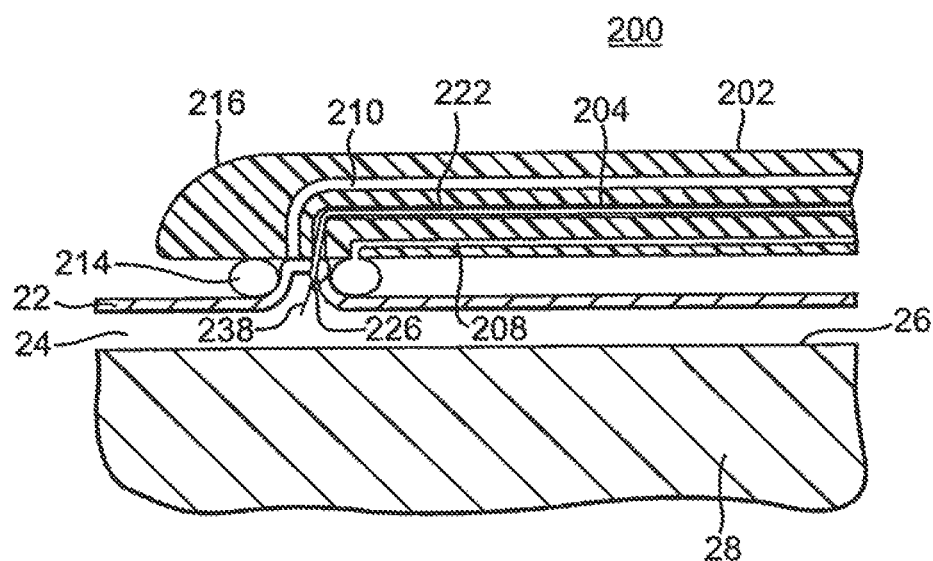
FIG. 12 is a side sectional view of the pericardial access system of FIG. 8 in which a guidewire has been introduced into the pericardial space.

At this point, the needle 204 is advanced through the secondary lumen 220 to penetrate the pericardium 22 and enter the enlarged pericardial space 234 (block 258), as shown in FIG. 11. A payload, such as a guidewire 238, may then be delivered through the needle port 230 into the enlarged region 234 of the pericardial space 24 (block 260), as shown in FIG. 12. Alternatively, the needle 204 is removed and the payload is introduced directly through the secondary lumen 222. Following completion of the procedure, needle 204 is withdrawn (block 262) and the negative pressure is eliminated, allowing the pericardium 22 to retract (block 264). Optionally, the inflation fluid or gas is reduced or removed, deflating the inflatable member (block 266). The pericardial access system 200 may then be removed from the heart 20 (block 268), leaving the payload in place.

When the inflatable member 214 is in a deflated configuration, for example, during insertion and removal, the pericardial access device 200 displays a lower profile. When inflated and after suction is applied, the inflatable member 214 defines a pericardial bleb, as is shown in FIG. 10, suitable for facilitating a variety of procedures. Furthermore, the inflatable member 214 may be inflated to an intermediate configuration defining a cavity of a different volume or configuration than in the fully inflated configuration. This allows the user to control the size or configuration of the region 234.

Although the secondary lumen 222 is shown in FIGS. 8-12 as having a nearly right angle curve proximal to the port 224, the secondary lumen 222 may be formed with varying angles adapted to point the needle 204 toward the pericardium 22. The angle may be greater or lower to increase or decrease the amount of force needed to penetrate the pericardium 22, or to facilitate navigation of the needle 204 therethrough. As shown in FIGS. 8 and 11, the needle 204 extends from a proximal end (not shown) to a sharp distal end 226. Needle 204 is hollow and terminates in a distal port 230 at or proximally adjacent to the distal end 226. The needle 204 may be adapted for receiving a payload such as a medical instrument, for example, a guidewire, or a fluid or gas.

Figure 13:
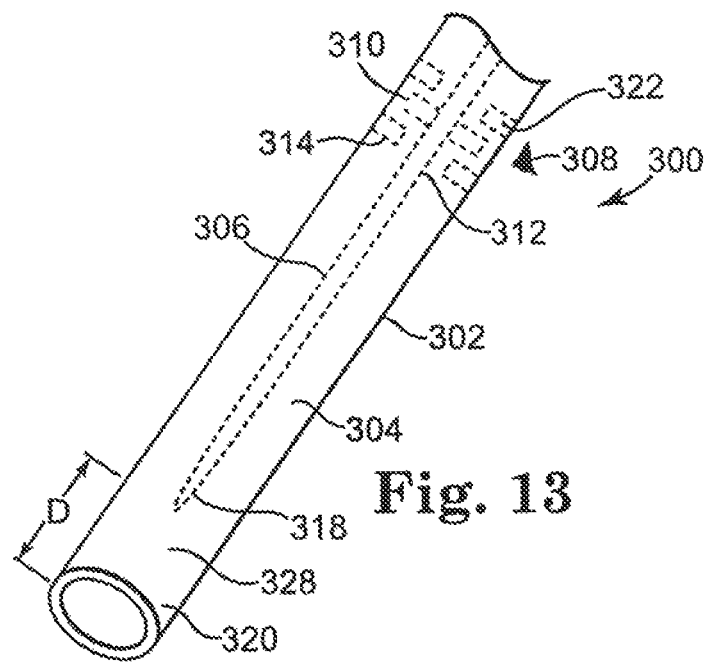
FIG. 13 is a perspective view of a pericardial access system in accordance with another embodiment of the present invention.
Figure 14:
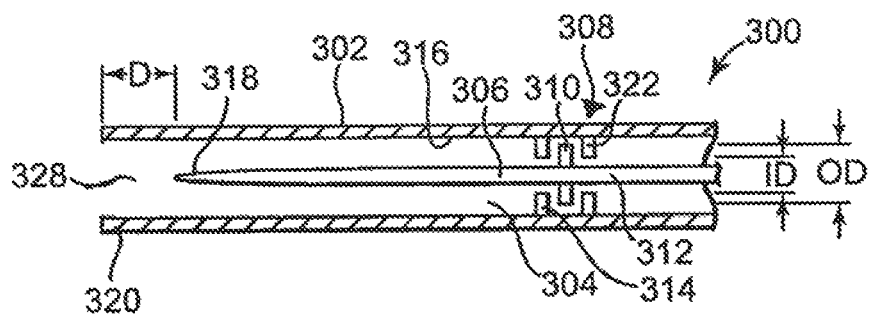
FIG. 14 is a side sectional view of the pericardial access system of FIG. 13.
Figure 15:
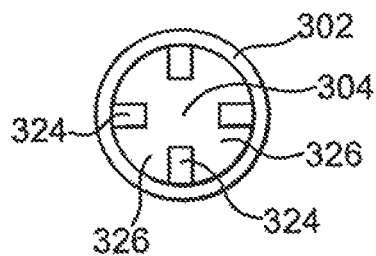
FIG. 15 is an end view of a shaft of the pericardial access system of FIG. 13.

FIGS. 13-15 show a pericardial access device 300 in accordance with another embodiment of the present invention. The pericardial access device 300 includes a tubular body 302 having an inner suction lumen 304 and a hollow needle 306 disposed within the suction lumen 304.

The needle is held in position by a flange structure 308 made up of a needle flange 310 extending about a proximal portion 312 of the needle 306 and a retention flange 314 extending inwardly from an inner wall 316 of the shaft 302. An outer diameter OD of the needle flange 310 is greater than an inner diameter ID of the retention flange 314. In this manner, the needle 306 is positioned or inserted within the suction lumen 304 such that a pointed distal end 318 of the needle 306 is positioned towards an open distal end or access port 320 of the shaft 302. The needle flange 310 engages the retention flange 314 and prevents further longitudinal displacement of the needle 306 with respect to the shaft 302. However, the needle 306 is free to rotate. A secondary retention flange 322 is positioned proximal to and spaced apart from the retention flange 314. The needle flange 310 is positioned therebetween to prevent inadvertent proximal displacement of the needle 306. In other embodiments, the needle 306 includes a secondary needle flange and the needle flange 310 and secondary needle flange are disposed on opposite sides of a single retention flange 314.

As is shown in FIG. 14, the retention flange 314 and secondary flange 322 are made up of multiple individual flanges 324 spaced apart from one another, defining spaces 326. Spaces 326 provides a passage for vacuum or suction to be applied throughout the suction lumen 304.

The needle flange 310 is positioned on the needle 306 such that the distal end 318 of the needle 306 is recessed by a distance D from the access port 320 of the shaft 302, forming a cavity or recessed space 328 between the distal end 320 of the shaft 302 and the distal end 318 of the needle 306. Thus, in a similar manner as described with respect to the pericardial access device generally shown in FIGS. 2-5, the access port 320 of the shaft 302 is engaged to a surface of the pericardium 22 and suction is applied. The shaft 302, and thus needle 306, is preferably positioned relative to the pericardium 22 to form an angle of about 90 degrees with respect to the pericardium 22. The access port 320 of the shaft 302 is sealed to the pericardium 22, and a portion of the pericardium 22 adjacent the access port 320 is drawn into the cavity 328 forming a pericardial bleb (not shown). The distance D is such that the portion of the pericardium 22 drawn into the cavity 328 engages the distal end 318 of the needle 306 and is pierced by the needle 306. The needle 302 can be rotated to facilitate piercing. Payloads, such as guidewires, can then be fed through the needle 306 into an enlarged space between the pericardium 22 and epicardium 26 to access the pericardial space 24 therebetween.

A pericardial access device according to any of the preceding embodiments may be used for a variety of procedures, including, for example, epicardial lead placement, cellular myoplasty, epicardial ablation, drug delivery, blind pericardial access, endoscopic pericardial access and endoscopic dissection of tissue reflections or adhesions. It can also be used for entering other spaces between anatomic tissue layers, including the peritoneum, vascular sheaths (for treatment of carotid disease or iliac/femoral artery disease) and the dura. A pericardial access system according to any of the preceding embodiments requires only a single surgical access point to locate the pericardium 22, form an enlarged region of pericardial space, and deliver a medical instrument into the pericardial space 24 without damaging the underlying tissues.

Various modifications and additions can be made to the exemplary embodiments discussed without departing from the scope of the present invention. Accordingly, the scope of the present invention is intended to embrace all such alternatives, modifications, and variations as fall within the scope of the claims, together with all equivalents thereof.

We claim:

1. A device for accessing a pericardial space of a heart, the device comprising:
   a shaft extending from a proximal end to a distal end, the shaft defining a cavity disposed near the distal end, and a suction lumen terminating in at least one distal suction port located within the cavity; and
   a hollow needle extending through the shaft and fixed in position relative to a longitudinal axis of the shaft such that the needle is prevented from moving longitudinally with respect to the shaft, the needle having a sharp distal end protruding into the cavity downwardly toward a heart surface at an angle with respect to a longitudinal axis of the shaft, wherein the suction lumen and the cavity are configured to draw pericardium into the cavity with suction and the needle is configured to pierce the pericardium as the pericardium is drawn into the cavity.

2. The device of claim 1 further comprising a guidewire adapted for advancing through a bore of the needle.

3. The device of claim 1 wherein the suction lumen terminates in a plurality of distal suction ports.

4. The device of claim 1 wherein the needle extends a distance of from about 0.5 to about 3 mm into the cavity.

5. The device of claim 1 wherein the angle is between about 15 and about 60 degrees.

6. The device of claim 1 wherein the angle is about 90 degrees.

7. The device of claim 1 wherein the cavity has a generally concave configuration with respect to the heart surface.

8. A device for accessing a pericardial space of a heart, the device comprising:
   a shaft having a proximal end and a distal end, the shaft sized such that the distal end can be brought into proximity with the pericardium while the proximal end is accessible from outside of the chest cavity, the distal end having an atraumatic tip;
   a cavity defined within the distal end of the shaft,
   a suction lumen in the shafting providing at least one distal suction port located within the cavity, the suction lumen and the cavity configured to draw pericardium into the cavity with suction; and
   a hollow needle within the shaft, the needle having a sharp distal end protruding within the cavity, the sharp distal end angled downward with respect to a longitudinal axis of the shaft, the sharp distal end of the needle wholly located within the cavity and fixed in position relative to a longitudinal axis of the shaft such that the sharp distal end is prevented from moving with respect to the shaft, the needle configured to pierce the pericardium as the pericardium is drawn into the cavity by suction.

9. The device of claim 8 wherein the cavity is proximal relative to the distal tip of the shaft.

10. The device of claim 8 wherein the needle extends a fixed distance from about 0.5 to about 3 mm within the cavity.

11. The device of claim 8 wherein the angle is about 90 degrees.

12. The device of claim 8 wherein the cavity has a generally concave shape.

13. The device of claim 8 wherein the needle extends to the proximal end of the shaft.

14. The device of claim 8 wherein the needle has an access port that is adapted to slidably receive a medical instrument.

* * * * *